United States Patent [19]
Tamazawa et al.

[11] Patent Number: 5,616,715
[45] Date of Patent: Apr. 1, 1997

[54] DIHYDROPYRIDINE-3, 5-DICARBOXYLIC ACID ESTER DERIVATIVES

[75] Inventors: Kazuharu Tamazawa; Tadao Kojima, both of Saitama; Hideki Arima, Tokyo; Yukiyasu Murakami, Saitama; Yasuo Isomura, Tokyo; Minoru Okada, Tokyo; Toichi Takenaka, Tokyo; Kiyoshi Takanobu, Saitama, all of Japan

[73] Assignee: Yamanouchi Pharmaceutical Co., Ltd., Tokyo, Japan

[21] Appl. No.: 491,793

[22] Filed: Jun. 19, 1995

Related U.S. Application Data

[62] Division of Ser. No. 238,537, May 5, 1994, Pat. No. 5,463,064, which is a division of Ser. No. 826,232, Jan. 23, 1992, Pat. No. 5,364,872, which is a continuation of Ser. No. 600,130, Oct. 17, 1990, abandoned, which is a continuation of Ser. No. 478,724, Feb. 9, 1990, abandoned, which is a continuation of Ser. No. 296,919, Jan. 11, 1989, abandoned, which is a continuation of Ser. No. 945,168, Dec. 22, 1986, abandoned, which is a continuation of Ser. No. 723,043, Apr. 15, 1985, abandoned.

[30] Foreign Application Priority Data

| Apr. 6, 1984 | [JP] | Japan | 59-114098 |
| Apr. 16, 1984 | [JP] | Japan | 59-75998 |
| Jul. 8, 1984 | [JP] | Japan | 59-165793 |

[51] Int. Cl.$^6$ .................................................. C07D 211/90
[52] U.S. Cl. ........................................................ 546/278.4
[58] Field of Search ............................................ 546/278.4

[56] References Cited

U.S. PATENT DOCUMENTS 4,463,176   7/1984   Dennis ................................... 546/208

OTHER PUBLICATIONS

Kawashima, Gen. Pharmacol., vol. 22(2), pp. 263–266, 1991.

Tamazawa, J. Med. Chem., vol. 29(12), pp. 2504–2511, 1986.

*Primary Examiner*—C. Warren Ivy
*Assistant Examiner*—D. Margaret M. Mach
*Attorney, Agent, or Firm*—Burgess, Ryan and Wayne

[57] ABSTRACT

A process is provided for producing diastereoisomer A or a pharmaceutically acceptable acid addition salt of 2,6-dimethyl-4-(3-nitrophenyl)-1,4-dihydropyridine-3,5-dicarboxylic acid 3-(1-benzylpyrrolidin-3-yl) ester 5-methyl ester which comprises subjecting a mixture of diastereoisomers A and B of 2,6-dimethyl-4-(3-nitrophenyl)-1,4-dihydropyridine-3,5-dicarboxylic acid 3-(1-benzylpyrrolidin-3-yl) ester 5-methyl ester to column chromatography using silica gel as a carrier and a mixture of ethyl acetate and acetic acid as an eluant, and then separating the acetate of diastereoisomer A from the eluate, or treating the acetate with a base, or further treating the resulting diastereoisomer A with a pharmaceutically acceptable acid.

2 Claims, No Drawings

DIHYDROPYRIDINE-3, 5-DICARBOXYLIC ACID ESTER DERIVATIVES

RELATED APPLICATIONS

The present application is a divisional application of application Ser. No. 08/238,537, filed May 5, 1994 now U.S. Pat. No. 5,463,064, which is a divisional application of application Ser. No. 07/826,232, filed Jan. 23, 1992 now U.S. Pat. No. 5,364,872, which is a continuation of application Ser. No. 07/600,130 filed Oct. 17, 1990, now abandoned, which is a continuation of Ser. No. 07/478,724 filed Feb. 9, 1990, now abandoned, which is a continuation of Ser. No. 07/296,919, filed Jan. 11, 1989, now abandoned, which in turn is a continuation of Ser. No. 06/945,168 filed Dec. 22, 1986, now abandoned, which in turn is a continuation of U.S. Ser. No. 06/723,043, filed Apr. 15, 1985, now abandoned.

FIELD OF THE INVENTION

This invention relates to diastereoisomer A of YM-09730, dextro-rotatory optical isomer thereof, and the pharmaceutically acceptable acid addition salts thereof. The invention further relates to a process of producing these compounds and also to medicaments using these compounds as an effective component.

BACKGROUND OF THE INVENTION

YM-09730 is a dihydropyridine-3,5-dicarboxylic acid ester derivative shown by the following chemical structure, the chemical name of which is 2,6-dimethyl-4-(3-nitro-pheny)-1,4-dihydropyridine-3,5-dicarboxylic acid 3-(1-benzylpyrrolidin -3-yl)ester 5-methyl ester.

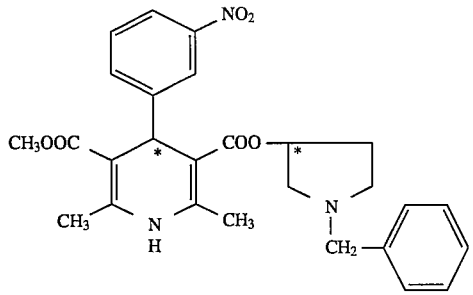

YM-09730 is the compound first synthesized by the researchers of the same company as the applicant of this application and it is reported that the compound has a vasodilating activity and a hypotensive activity, and also shows prolonged effect of about these activities (U.S. Pat. No. 4,220,649; U. K. Patent No. 2,014,134, etc.,).

YM-09730 has two asymmteric carbon atoms and it is assumed from the stereochemical view point that there are isomers based on these asymmeteric carbon atoms but there are no descriptions about these isomers in the above-described patents and the existence of these isomers was not confirmed.

SUMMARY OF THE INVENTION

The inventors have first succeeded in separating diastereoisomers A and B of YM-09730 and the optical isomers of them and have discovered that isomer A (the diastereoisomer A and the dextro-rotatory optical isomer thereof are together referred to as isomer A unless specifically indicated) has greatly excellent specific pharmaceutical effects as compared to isomer B (the diastereoisomer B and the optical isomer thereof are together referred to as isomer B unless specifically indicated) or to a mixture (YM-09730) of both isomers A an B and the inventors have succeeded in attaining the present invention based on the discovery. In this case, the melting point of the hydrochloride of the diastereoisomer A is 200° to 206° C. (decomp.) and the melting point of the hydrochloride of the dextro-rotatory optical isomer thereof is 223° to 230° C. (decomp.). Accordingly, the subject of the compounds of this invention is isomer A, specified by the melting point of the hydrochloride thereof, of YM-09730 and the pharmaceutically acceptable acid addition salts Thus, according to this invention, there is provided isomer A of 2,6-dimethyl-4-(3-nitro-phenyl)-1,4-dihydropyridine-3,5-dicarboxylic acid 3-(1-benzylpyrrolidin -3-yl)ester 5-methyl ester, the melting point of the hydrochloride of diastereoisomer A being 200° to 206° C. (decomp.), and the pharmaceutically acceptable acid addition salts thereof.

DETAILED DESCRIPTION OF THE INVENTION

Now, the phamaceutically acceptable acid addition salts in this invention include malonates, oxalates, p-nitrobenzoates, 2-ketoglutarates, maleates, 1-malates, hydrochlorides, sulfates, p-toluenesulfonates, phosphates and succinates.

As shown in the phrmacological experimental results described hereinafter, the isomer A of this invention or the pharmaceutically acceptable acid addition salts thereof show an area ratio of 15 to 38 times that of diastereoisomer B and of 14 to 35 times that of an equivalent mixture of these diastereoisomers in the increasing rate of an amount of a coronary blood stream by the direct administration into the coronary arteries, which shows a high affinity of isomer A of this invention for the coronary arteries.

On the other hand, isomer B showed almost the same effect as that of the equivalent mixture of the isomers. This means that the pharmacological action of YM-09730 is not a simple mean value of the physical mixture ratios of these isomers. Also, it is a new pharmacological discovery found by the inventors that isomer A and the pharmaceutically acceptable acid addition salts thereof have a high affinity for coronary arteries and increase the possibility of the utilization of the compounds of this invention as medicaments.

Then, the production process for isomer A of this invention or the pharmaceutically acceptable acid addition salts thereof will be explained below.

I. Production of Diastereoisomer A

As described above, there are no descriptions about the isomers of YM-09730 in aforesaid U.S. Pat. No. 4,220,649 and U. K Patent No. 2,014,134 and the production of these isomers was not reported in any reports published thereafter. A pair of diasetereoisomers differ in absolute value of rotatory power as well as in the whole physical and chemical properties different from general optical antipodes and hence if these properties are not clarified, each isomer cannot be produced based on the difference in these properties.

The inventors prepared YM-09730 by the Hantzch's synthesis process of dihydropyridine (Ann. Chim., 215, 1(1882)) shown in Reference example described hereinafter and could know that YM-09730 was an equivalent mixture of diastereoisomer A and diastereoisomer B. Also, as the result of various investigations on the process of obtaining diastereoisomer A from the mixture of the isomers based on this discovery, diastereoisomer A could be obtained by the following procedures (a) The mixture of the diastereoisomers was subjected to column chromatography using silica gel as the carrier and a mixed solution of ethyl acetate and acetic acid as the eluent and diastereoisomer A was obtained from the initial eluate and diastereoisomer B from the latter eluate. These two isomers are obtained from novel compounds first discovered by the inventors.

As silica gel for use in the production process as a carrier for column chromatography, any silica gel which is usually used for column chromatography can be used without any restriction. Also, there is no particular restriction about the mixing ratio of ethyl acetate and acetic acid in the mixed solvent for use as the eluent but usually the mixed solvent containing a small amount of acetic acid is used. The mixing ratio is 30 to 50 v/v for ethyl acetate and about 1 to 10 v/v for acetic acid and if the content of acetic acid is lowered, the eluting time of the desired compound is prolonged. The elution rate and the processing temperature can be properly selected.

(b) Also, in other process than the above process, the inventors succeeded in producing the acid addition salt of diastereoisomer A by inducing the mixture of the distereoisomers to specific acid addition salts and subjecting the mixture of the salts to a fractional recrystallization.

The acid addition salts for use in the production process are malonate, p-nitrobenzoate, maleate, etc.

These acid addition salts are crystalline salts and the solubility in an organic solvent differs between diastereoisomer A and diasetereoisomer B. Thus, these properties can be utilized for producing diasetereoisomer A by a fractional recrystallization. A particular suitable acid addition salt is malonate. In the case of using the malonate, crystals having a very high content of diastereoisomer A can be obtained by one recrystallization. As a solvent for use in the production process, there are methanol, ethanol, acetone, acetonitrile, etc.

The acid addition salt of diastereoisomer A of YM-09730 obtained by the above-described process can be acid-exchanged into a desired acid addition salt by once inducing the salt into a free form and reacting with other acid.

II. Production of Dextro-rotatory Optical Isomer A (a) The dextro-rotatory optical isomer of diastereoisomer A can be obtained by reacting the mixed free bases of diastereoisomers A and B or the free base of the acid addition salt of diastereoisomer A of YM-09730 obtained by the production process I described above with L-(−)-malic acid and then subjecting the product to optical resolution by an ordinary manner as described hereinafter.

(b) Also, in a more preferred production process the dextro-rotatory optical isomer of diastereoisomer A, dextro-rotatory optical isomer is separated from YM-09730 (a mixture of the dextro-rotatory optical isomer of diastereoisomer A and the levo-rotatory optical isomer of diastereoisomer B) shown by formula (I)

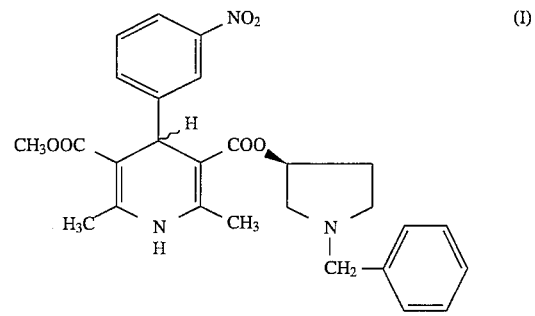

(wherein the wavelike bond means an α-bond or β-bond and the bond shown by the dense arrow means a β-bond), wherein the bond at 3-position of the pyrroldine ring is a specific β-bond.

The raw material compound (I) can be produced (i) by reacting m-nitrobenzaldehyde shown by formula (II)

(S)-3-acetoacetoxy-1-benzylpyrrolidine shown by formula (III)

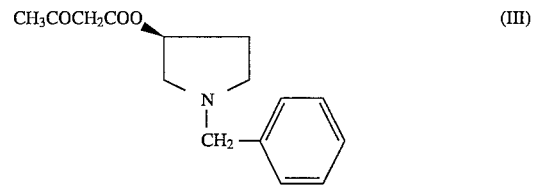

and 3-aminocrotonic acid methyl ester shown by formula (IV)

$$CH_3\underset{NH_2}{C}=CHCOOCH_3; \qquad (IV)$$

(ii) by reacting m-nitrobenzaldehyde shown by formula (II) above, acetoacetic acid methyl ester shown by formula (V)

$$CH_3COCH_2COOCH_3 \qquad (V)$$

and (S)-3-(3-aminocrotonoyloxy)-1-benzylpyrrolidine shown by formula (VI)

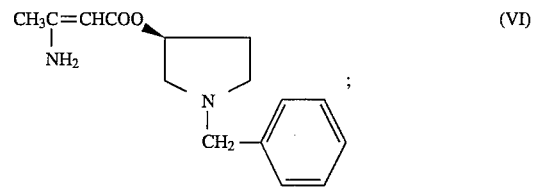

(iii) reacting (S)-1-benzyl-3-[2-(m-nitrobenzylidene)-acetoacetoxy]pyrrolidine shown by formula (VII)

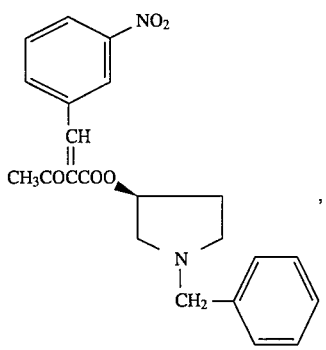

obtained by previously reacting m-nitrobenzaldehyde shown by formula (II) above and (S)-3-acetoacetoxy-1-benzylpyrrolidine shown by formula (III) above and 3-aminocrotonic acid methyl ester shown by formula (IV) above; or (iv) reacting 2-(m-nitrobenzylidene)acetoacetic acid methyl ester shown by formula (VIII)

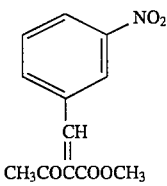

obtained by previously reacting m-nitrobenzaldehyde shown by formula (II) above and acetoacetic acid methyl ester shown by formula (V) above and (S)-3-(3-aminocrotonoyloxy)-1-benzylpyrrolidine shown by formula (VI) above.

These reaction proceed without use of solvent but it is advantageous to perform the reaction in a solvent which does not take part in the reaction, such as an alcohol, dioxane, dimethylformamide, dimethylsulfoxide, acetonitrile, water, etc. The reaction is performed by heating a mixture of an almost equimolar amount of each component.

In addition, the compound of formula (IV) or the compound of formula (VI) described above can be obtained by reacting the compound of formula (V) or the compound of formula (III) with ammonium acetate and acetic acid in benzene and azeotropically dehydrating the product. Also, the compound of formula (IV) or compound of formula (VI) thus obtained is supplied to reaction (i) or (ii) described above after being isolated or without being isolated from the reaction mixture.

Also, the compound of formula (VII) or the compound of formula (VIII) which is the reaction produce in the first step reaction process of process (iii) or (iv) can be supplied to the last step process after being isolated once or without being isolated.

The mixture of the dextro-rotatory optical isomer of diastereoisomer A of YM-09730 and the levo-rotatory optical isomer of diastereoisomer B thus obtained is subjected to column chromatography using silica gel as the carrier and a mixture of ethyl acetate and acetic acid as the eluent to separate the dextro-rotatory optical isomer of diastereoisomer A of YM-09730, or the mixture described above is reacted with L-(–)-malic acid to form the mixture of the L-(–)-malate of the dextro-rotatory optical isomer of diastereoisomer A and the L-(–)-malate of the levo-rotatory optical isomer of diastereoisomer B and by fractionally recrystallizing the mixture, the L-(–)-malate of the dextro-rotatory optical isomer of diastereoisomer A can be obtained.

In the separation by column chromatography, the dextro-rotatory optical isomer of diastereoisomer A is obtained from the first eluate and the levo-rotatory optical isomer of diastereoisomer B can be obtained from the latter eluate.

As silica gel for use as the carrier, any silca gel which is generally used for column chromatography can be used without particular restriction. There is no particular restriction about the mixing ratio of ethyl acetate and acetic acid for use as the eluent but the mixed solvent containing a small amount of acetic acid is preferred. It is advantageous that the mixing ratio is 30 to 50 v/v for ethyl acetate and about 1 to 10 v/v for acetic acid and when the content of acetic acid is further lowered, the eluting time for the desired compound is prolonged.

The eluting time and the processing temperature may be properly selected.

On the other hand, the process of using L-(–)-malic acid can also utilized for the separation of the dextro-rotatory optical isomer of diastereoisomer A by recrystallization since the L-(–)-malate of the dextro rotatory optical isomer of diastereoisomer A of YM-09730 is crystalline. As the solvent for use in the fractional recrystallization, there are methanol, ethanol, acetone, acetonitrile, etc.

The L-(–)-malate of the dextro-rotatory optical isomer of diastereoisomer A thus obtained can be used for medicament as it is, but can be induced into the acetate or other suitable salt, if necessary, by treating the L-(–)-malate with a base to form a free form and treating the product with a proper acid.

In addition, by hydrolyzing the levo-rotatory optical isomer of diastereoisomer B separated in the above process, (S)-(–)-1-benzyl-3-hydroxypyrrolidine can be recovered and hence the pyrrolidine can be reused as the raw material for producing the compound of formula (I).

The pharmacological activities, acute toxicity and clinical doses of isomer A are explained as follows.

(1) Coronary Vasodilating Effect in Anesthetized Dogs

In open-chest dogs anesthetized with 30 mg/kg i.v. of pentobarbital sodium, arterial blood from the carotid artery was led to circumflex branch of the left coronary artery by a extracorporeal loop. A servocontrolled pure (model 1215D, Harvard Apparatus) was incorporated in the circuit to maintain a constant perfusion pressure of 120 mmHg by means of a pump controller (SCS-22, Data Graph Co., Tokuya Tukada et al., Folia Pharmacol. Japon, 74, 59p, 1978). An electromagnetic flow probe of extracorporeal type (MF-25, Nihon Koden) was also inserted in the circuit to record coronary blood flow. A dose of 1 μg of the compound was administered directly into the coronary artery and then coronary blood flow was monitored until the blood flow returned to the pretreatment value. And then, the area under the percent increase in coronary blood flow after intracoronary injection of 1 μg of the compound was calculated and used as an index of the overall increase in coronary blood flow. Results are shown in Table 1.

TABLE 1

| | Coronary vasodilating activity in anesthetized dogs | |
|---|---|---|
| | Overall increase in coronary blood flow at 1 μg (%, min.) | Duration of the action |
| Diastereoisomer A (dl form) hydrochloride | 1816 ± 377 | 60 |
| Diastereoisomer A (d form) hydrochloride | 4559 ± 894 | 120 |
| Diastereoisomer A (l form) hydrochloride | 120 ± 21 | 5 |
| Diastereoisomer B (dl form) hydrochloride | 120 ± 28 | 5 |
| Equivalent mixture of the hydrochlorides of diastereoisomers A (dl form) and B (dl form) | 129 ± 47 | 10 |

When directly administered into the coronary artery, the overall increase in coronary blood flow after 1 μg of the isomer A hydrochloride was approximately 15 to 38 times higher than those after an identical dose of the isomer B hydrochloride and the equivalent mixture of these isomers, indicating that the isomer A hydrochloride possesses a high affinity for the coronary artery. Furthermore, duration of the coronary vasodilating activity after the isomer A hydrochloride was clearly longer than those after the isomer B hydrochloride and the equivalent mixture of these isomer. Such a high affinity for the coronary artery and long durability indicate that the isomer A hydrochloride is useful for the treatment of coronary artery disease such as angina pectoris.

(2) Hypotensive Effect in Anesthetized Rats

Blood pressure was measured in urethane-anesthetized rats. The compound was intravenously administered in an increasing dose manner at an interval of 20 minutes. The doses of the compounds required to lower mean blood pressure by 30 mmHg (ED 30 mmHg) was calculated from the dose-response curves and summarized in Table 2.

TABLE 2

| Hypotensive activity in anesthetized rats | |
|---|---|
| | ED30 mmHg (mg/kg i.v.) |
| Diastereoisomer A (dl form) hydrochloride | 0.002 |
| Diastereoisomer B (dl form) hydrochloride | 0.14 |

As can be seen in Table 2, the hypotensive activity of the diastereoisomer A hydrochloride was about 70 times more potent than that of the diastereoisomer B hydrochloride.

(3) Acute Toxicity in Mice

Six weeks old and male ICR mice weighing 27 to 29 g were used. The compound was suspended in 0.5% methylcellulose solution and administered orally to mice. The $LD_{50}$ values of the compounds were calculated by the method of Litchfield & Wilcoxon (Journal of Pharmacol. & Exp. Therap., 96, 99–113, 1949) and summarized in Table 3.

TABLE 3

| Acute toxicity in mice | |
|---|---|
| | $LD_{50}$ mg/kg p.o. |
| Diastereoisomer A (dl form) hydrochloride | 295 (242–360) |
| Diastereoisomer A (d form) hydrochloride | 190 (158–228) |

(4) Clinical Doses

The clinical doses of the compounds of this invention depend on the body weight and the condition of disease of patients. The optimal doses are usually 0.1 to 2 mg for intravenous injection and 5–20 mg once or twice a day for oral administration.

Then, the compounds of this invention, the production process thereof, and the medicaments using these compounds are explained by the following examples and formulation examples. In addition, the production examples of a mixture of diastereoisomer A and diastereoisomer B which is used as the raw material is explained as Reference Example 1 and the production example of (S)-(–)-1-benzyl-3-hydroxypyrrolidine which is also used as the raw material in the examples is explained as Reference Examples 2–4.

REFERENCE EXAMPLE 1

In 5 ml of isopropanol were dissolved 1.51 g (0.01 mole) of 3-nitrobenzaldehyde, 2.61 g (0.01 mole) of 1-benzyl-3-acetoacetoxypyrrolidine, and 1.15 g (0.01 mole) of 3-aminocrotonic acid methyl ester and the solution thus obtained was refluxed for 8 hours. Then, the solvent was distilled off under reduced pressure, the residue thus formed was dissolved in chloroform, the solution was washed, in succession, with diluted hydrochloric acid, water, a saturated aqueous sodium hydrogencarbonate solution, and dried over anhydrous magnesium sulfate. Then, the solvent was distilled off under reduced pressure to provide 4.91 g of 2,6-dimethyl-4-(3-nitrophenyl)-1,4-dihydropyridine-3,5-dicarboxylic acid 3-(1-benzylpyrrolidin-3-yl)ester 5-methyl ester as a caramel form.

The formation ratio of the diastereoisomer thus obtained as the crude base was analyzed by reversed-phase ion-pair high-performance liquid chromatography (HPLC) under the conditions shown below. The ratio of diastereoisomer A (retention time 28 min): diastereoisomer B (retention time 29 min.) was 1:1.

Column: 4.6 mm×300 mm packed with Nucleosil® 5 $C_{18}$, column temperature: 30° C. mobile phase: acetonitrile –0.05 mole potassium dihydrogenphosphate (pH 3) (20:80 v/v) containing tetra-n-pentylammonium bromide (3 mmole) as counter ion, Flow rate: 0.9 ml/min., monitor: ultraviolet detector (λ254 nm).

In addition, by nuclear magnetic resonance analysis, diastereoisomer A and diastereoisomer B were confirmed to have a different chemical shift with respect to methylene protons of N-benzyl group of YM-09730. By measurement in heavy methanol $d_4$ ($CD_3OD$) with Jeol NMR- spectrometer FX-90Q, isomer A and isomer B show the singlet signals corresponding to two protons at 4.40 ppm and 4.30 ppm, respectively.

REFERENCE EXAMPLE 2

(1) In 66 ml of acetone were dissolved 17.7 g of dl-1-benzyl-3-hydroxypyrrolidine and 15.2 g of D-(–)-mandelic acid with heating and the solution was allowed to stand overnight at 4° C. to deposit crystals. Then, 8.5 g of the crystals thus deposited were collected and recrystallized from 26 ml of acetone to provide 5.1 g of D-(–)-mandelate of (S)-(–)-1-benzyl-3-hydroxypyrrolidine. The specific rotation $[\alpha]_D^{20}$ was –45.5° C. (c=1, methanol. When the recrystallization was further repeated, the specific rotation was not changed. The melting point was 101°–102° C.

By nuclear magnetic resonance analysis signal of N-CH$_2$-Ph thus obtained mandelate of (S)-(–)-form compound was observed at 4.03 ppm (singlet, 2H). The signal of AB-type quartet (J=12.5 Hz) at 4.01 ppm of the (R)-(–) form was not observed.

(2) In 50 ml of chloroform was dissolved 22 g of D-(–)-mandelate of (S)-(–)-1-benzyl-3-hydroxypyrrolidine and the chloroform solution thus formed was washed with a solution of 14.4 g of sodium carbonate in 90 ml of water and dried over anhydrous magnesium sulfate. Then, after distilling off chloroform, the residue was distilled under reduced pressure to provide 11.5 g of S-(–)-1-benzyl-3-hydroxypyrrolidine. The boiling point was 109° C./0.65 mmHg and $[\alpha]_D^{20}$ was –3.77° (c=5, methanol ).

REFERENCE EXAMPLE 3

By reacting 75 g of (S)-(–)-malic acid and 75 ml of benzylamine for 3 hours at 170° C., 52.7 g of (S)-(–)-1-benzyl-3-hydroxy-succinimide (melting point 99°–101° C., specific rotation $[\alpha]_D^{20}$ -51.1°, (c=1, methanol)) was obtained. In 340 ml of anhydrous tetrahydrofuran was suspended 9.73 g of lithium aluminum hydride and a solution of 20.5 g of the above-described imide in 200 ml of anhydrous tetrahydrofuran was added dropwise to the suspension under ice-cooling. After refluxing the mixture for 3 hours, 100 g of sodium sulfate decahydrate was added to the mixture under ice-cooling and the resultant mixture was stirred overnight under ice-cooling. Insoluble solids were filtered off, the solvent was evaporated under reduced pressure from the filtrate, and the residue was distilled under reduced pressure to provide 13.8 g of (S)-(–)-1-benzyl-3-hydroxypyrrolidine having a boiling point of 109° to 115° C./0.8 mmHg and specific rotation $[\alpha]_D^{20}$ of –3.0° (c=5, methanol). It was confirmed that the (S)-(–)-form obtained above contained 10% R-(+)-1-benzyl-3-hydroxypyrrolidine by proton nuclear magnetic resonance analysis of the 3-position using a shift reagent Eu-TFMC(III). The product was induced to the D-(–)-mandelate as reference Example 2. The mandelate $[\alpha]_D^{20}$ –45.2° (c=1, MeOH) obtained by recrystallizing from 3 times by volume of ethanol and then 6 times by volume of ethanol-toluene (1:5 v/v, was treated with chloroform and a solution of aqueous sodium carbonate as Reference Example 2 to give 8.6 g of (S)-(–)-1-hydroxypyrrolidine; boiling point 115° to 120° C./1.2 to 1.5 mmHg, $[\alpha]_D^{20}$ –3.77° (c=5, methanol).

REFERENCE EXAMPLE 4

To 50 ml of 9-borabicyclo [3,3,1] nonane (0.5M tetrahydrofuran solution) was added 3.4 g of 2-(–)-pinene and the mixture was stirred for 5 hours at 60° C. After cooling the mixture to room temperature, 1.75 g of 1-benzyl-3-pyrrolidinone was added thereto. After stirring the mixture for 4 days at room temperature, 1.3 ml of acetaldehyde was added thereto at 0° C. Then, the solvent was distilled off under reduced pressure from the reaction mixture and 20 ml of ether was added to the residue. After cooling the mixture to 0° C., 1.5 ml of 2-aminoethanol was added thereto and the resultant mixture was stirred. Precipitates thus formed were filtered off. The ether solution recovered as the filtrate was extracted with 1N hydrochloric acid and the hydrochloric acid layer thus formed was made basic with sodium carbonate and extracted with dichloromethane. The extract thus formed was dried by anhydrous magnesium sulfate and concentrated to provide 1.1 g of a crude product. Then, by subjecting the crude product to distillation under reduced pressure, 0.6 g of a purified product was obtained. The boiling point thereof 106° C./0.9 mmHg. (S)-(–)-1-benzyl-3-hydroxypyrroidine thus obtained was 30% e. e. analyzed by the nuclear magnetic resonance spectra with respect to the proton at the 3-position using a shift reagent Eu-TFMC(III).

PRODUCTION EXAMPLE OF DIASTEREOISOMER A

EXAMPLE 1

In 25 ml of chloroform was dissolved 4.91 g of the crude free base of YM-09730 obtained in Reference Example 1 and after adding thereto 15 ml of 10% hydrochloric acid followed by stirring well, the organic phase thus formed was separated. The organic layer was treated again by the same manner as above with 10 ml of 10% hydrochloric acid, and after drying the treated product with anhydrous magnesium sulfate, the solvent was distilled off under reduced pressure. The residue thus obtained was dissolved in 10.4 ml of acetone and the solution was allowed to stand to provide 3.5 g of the hydrochloride of YM-09730 as crystals. The product was disssolved in 1.8 ml of methanol and recrystallized with the addition of 8 ml of acetone. By repeating once, 2.38 g of the hydrochloride of YM-09730 was obtained. The ratio of diastereoisomer A: diastereoisomer B in the hydrochloride was 65.6:34.4 by HPLC. In 25 ml of chloroform was dissolved 2.15 g of the aforesaid salt, the solution thus obtained was washed twice each time with 15 ml of a saturated aqueous sodium hydrogencarbonate solution, and the organic layer thus formed was collected and dried over anhydrous magnesium sulfate Then, the solvent was distilled off under reduced pressure and 2 g of a free base thus obtained was subjected to silica gel column chromatography (column: LiChroprep$^R$ Si60, C size, Eluent ethyl acetate-acetic acid=30:5 v/v) to provide the oily acetate of diastereoisomer A.

The product was dissolved in 10 ml of chloroform, the solution thus formed was washed, in succession, with 10 ml of a saturated aqueous sodium hydrogencarbonate solution, 10 ml of water, and 10 ml of 10% hydrochloric acid, and dried with anhydrous magnesium sulfate. Then, the solvent was distilled off under reduced pressure and the residue thus obtained was treated with 0.8 ml of acetone to provide 0.4 g of the hydrochloride of diasteroisomer A.

EXAMPLE 2

In 15 ml of acetonitrile were dissolved 4.91 g of the crude free base of YM-09730 obtained in Reference Example 1 and 1.04 g of malonic acid and the solution thus obtained was allowed to stand overnight at 0° to 5° C. Crystals thus formed were collected by filtration, washed with a small amount of cold acetonitrile to provide 2.03 g of the malonate of YM-09730. (Ratio of diastereoisomer A:B was 89.1:10.9). The product was recrystallized twice each time from 25 times by volume of methanol to provide 1.0 g g of the malonate of 100% diastereoisomer A of YM-09730.

EXAMPLE 3

In 15 ml of methanol were dissolved 4.91 g of the crude free base of YM-09730 obtained in Reference Example 1 and 1.04 g of malonic acid by heating and the solution thus formed was allowed to stand overnight at 0° to 5° C. Crystals thus deposited were collected by filtration, washed with methanol, and dried under reduced pressure to provide 1.88 g of the malonate of YM-09730. The ratio of diastereoisomers A:B of the crystals thus obtained was 90.7:9.3. The crystals were recrystallized twice from methanol to provide the malonate of diasetereoiosmer A containing no isomer B.

EXAMPLE 4

By following the same procedure as in Example 3 using acetonitrile in place of methanol, 2.03 g of a malonate was obtained. The ratio of diastereoisomers A:B was 89.1:10.9. The product was recrystallized from 25 times by volume of methanol to provide 1.57 g of the malonate of diastereoisomers A and B at a ratio of 99.5:0.5. Furthermore, by recrystallizing the product from 25 times by volume of methanol, 1.27 g of the maolonate of YM-09730 wherein the presence of diastereoisomer B was not detected by high performance liquid chromatography was obtained. In 5 ml of chloroform was suspended 1.27 g of the malonate, the chloroform suspension was treated, in succession, twice each time with a saturated aqueous sodium carbonate solution, twice each time with 2.5 ml of water, and then twice each time with 2.5 ml of 10% hydrochloric acid, the chloroform solution thus washed was dried over anhydrous magnesium sulfate, filtered, and evaporated to dryness under reduced pressure. The residue thus formed was dissolved in 2 ml of acetone and the solution was allowed to stand to deposit 1.09 g of the hydrochloride of diastereoisomer A of YM-09730.

EXAMPLE 5

In 5 ml of chloroform was suspended 595 mg of the malonate of distereoisomer A of YM-09730 and the suspension thus obtained was treated twice each time with 2.5 ml of a saturated aqueous sodium hydrogen carbonate solution and then twice each time with 5 ml of water. The chloroform solution thus obtained was dried over anhydrous magnesium sulfate and evaporated to dryness under reduced pressure to provide 491 mg of the free base of diastereoisomer as a caramel. The product and 126 mg of oxalic acid dihydrate were dissolved in 3 ml of acetone, the solution thus formed was allowed to stand at 4° C., and the crystals thus deposited were collected by filtration to provide 400 mg of the oxalate of diastereoisomer A of YM-09730.

EXAMPLE 6

By following the same procedure using 146 mg of 2-ketoglutaric acid in place of oxalic acid in Example 5, 250 mg of the 2-ketoglutarate of diastereoisomer A of YM-09730 was obtained.

EXAMPLE 7

By following the same procedure using 167 mg of p-nitrobenzoic acid in place of oxalic acid in Example 5, 530 mg of p-nitrobenzoate of diastereoisomer A of YM-09730 was obtained.

EXAMPLE 8

By following the same procedure as in Example 5 using 116 mg of maleic acid in place of oxalic acid, 300 mg of the maleate of diastereoisomer A of YM-09730 was obtained.

EXAMPLE 9

In 2 ml of acetone was dissolved 491 mg of diastereoisomer A of 09730 and after adding thereto 1 ml of a methanol solution of 1 mole of phosphoric acid, the solution was allowed to stand at 4° C. Crystals thus deposited were collected by filtration to provide 480 mg of the phosphate of diastereoisomer A of YM-09730.

The properties of the desired compounds obtained in Examples 1 to 9 are shown in the following table.

| Desired Compound | Composition Formula | M. P. | Properties Elemtal analysis | | | |
|---|---|---|---|---|---|---|
| | | | C (%) | H (%) | N (%) | Cl (%) |
| Phosphate | $C_{27}H_{29}N_3O_6$·$H_3PO_4$·½$H_2O$ | 216–218 | 54.39 54.18 | 5.56 5.56 | 6.96 7.02 | |
| Hydrochloride | $C_{27}H_{29}N_3O_6$·HCl | 203–205 (decomp.) | 61.59 61.42 | 5.71 5.73 | 8.08 7.96 | 6.90 6.71 |
| p-Nitrobenzoate | $C_{27}H_{29}N_3O_6$·$C_7H_5NO_4$·¼$H_2O$ | 150–151 | 61.58 61.58 | 5.20 5.24 | 8.32 8.32 | |

-continued

| | | | | | |
|---|---|---|---|---|---|
| Maleate | C₂₇H₂₉N₃O₆·<br>C₄H₄O₄ | 168–169 | 61.40<br>61.28 | 5.49<br>5.47 | 6.85<br>6.92 |
| 2-Keto-<br>glutarate | C₂₇H₂₉N₃O₆·<br>C₅H₄O₃ | 160–161 | 60.36<br>60.28 | 5.48<br>5.53 | 6.52<br>6.59 |
| Oxalate | C₂₇H₂₉N₃O₆·<br>C₂H₂O₄ | 179–180 | 60.14<br>60.36 | 5.62<br>5.70 | 6.93<br>6.88 |
| Malonate | C₂₇H₂₉N₃O₆·<br>C₃H₄O₄ | 181.5–<br>182.5<br>(decomp.) | 59.89<br>60.50 | 5.37<br>5.58 | 7.23<br>7.06 |

(Upper: Found values)
(Lower: Calculated values)

Hydrochloride: NMR(in CD₃OD, TMS internal standard, δppm)

1.80–2.70(2H, broad m, C₄'—H₂)
2.32, 2.34(6H, s, C₂,₆—CH₃)
3.0–4.0(4H, m, C₂',₅'—H₂)
3.63(3H, s —COOCH₃)
4,40(2H, s, —CH₂-φ)
5.08(1H, s, C₄—H)
5.30(1H, m, C₃'—H)
7.30–8.20(9H, m, H of benzene ring)

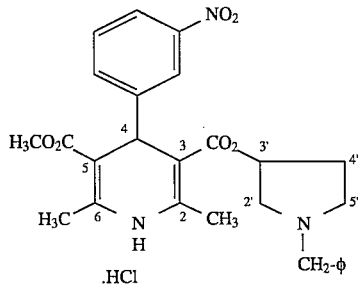

EXAMPLE 10

In 5 ml of chloroform was suspended 1.5 g of the malonate of diastereoisomer A obtained in Example 3 or 4 and the suspension was treated, in succession, twice each time with 3 ml of a saturated aqueous sodium hydrogen carbonate solution and then twice each time with 3 ml of water. The chloroform solution was dried over anhydrous magnesium sulfate and then the solvent was distilled off under reduced pressure. To the residue thus obtained was added 6 ml of ethanol and the mixture was allowed to stand overnight at 5° C. to obtain 0.86 g of crystals of the free base of diastereoisomer A of YM-09730.

Melting point 145° to 148° C.

| Elemental analysis for (C₂₇H₂₉N₃O₆) | | | |
|---|---|---|---|
| | C (%) | H (%) | N (%) |
| Calculated | 65.98 | 5.95 | 8.55 |
| Found | 66.04 | 6.00 | 8.53 |

NMR(in CDCl₃, TMS internal standard, δppm):

1.40 to 2.96(6H, m, C₂',₄',₅'—H₂)
2.34, 2.36(6H, s, C₂,₆—CH₃)
3.65(5H, s, —COOCH₃ and —CH₂φ)
5.10(1H, s, C₄—H)
5.12(1H, m, C₃'—H)
5.78(1H, broad s, NH)
7.18 to 8.25(9H, m, H of benzene ring)

-continued

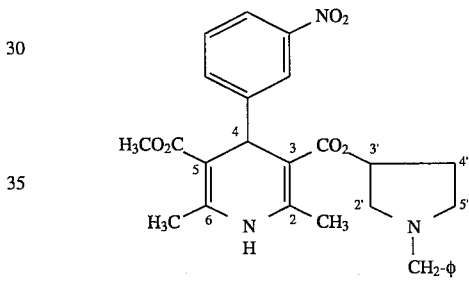

Production of Dextro-rotatory A Isomer

EXAMPLE 11

(1) In 15 ml of acetonitrile were dissolved 4.91 g of the crude free base obtained in Reference Example 1 above and 1.04 g of malonic acid and the solution was allowed to stand overnight at 0° to 5° C. Crystals thus deposited were collected by filtration (2.03 g) and recrystallized twice each time from 25 times by volume of methanol to provide 1.27 g of the malonate of diastereoisomer A of YM-09730 containing no diastereoisomer B. The melting point thereof was 181.5° C. to 182.5° C. (decomp.). In 5 ml of chloroform was suspended 1.27 g of the malonate thus obtained and the suspension was washed, in succession, twice each time with 2.5 ml of a saturated aqueous sodium hydrogencarbonate solution, once with 2.5 ml of water, and then twice each time with 2.5 ml of an aqueous 10% hydrochloric acid solution. The chloroform solution was dried over anhydrous magnesium sulfate and evaporated to dryness under reduced pressure. The residue thus formed was dissolved in 2 ml of acetone, the solution was allowed to stand, and 1.09 g of the hydrochloride of diastereoisomer A of YM-09730 thus deposited was collected.

(2) By treating 4.67 g of the hydrochloride diastereoisomer A of YM-09730 obtained in the above step with saturated aqueous sodium hydrogencarbonate, 4.35 g of the free base thereof was obtained and then 4.35 g of the free base thus obtained and 1.18 g of L-(−)-malic acid were dissolved in 28 ml of ethanol with heating and the solution was allowed to stand overnight at 0° to 5° C. Crystals thus deposited were collected by filtration and dried to provide 2.43 g of the L-(−)-malate of the dextro-rotatory optical isomer of diastereoisomer A of YM-09730. The crystals were recrystallized from 85 ml of ethanol to provide 2.21 g of the L-(−)-malate. The specific rotation $[\alpha]_D^{20}$ was +82.2° (c=0.5, methanol). When the product was recrystallized from ethanol, the change of the specific rotation was not observed.

Melting point 190° to 191° C. (decomp.).

| Elemental analysis (for $C_{27}H_{29}N_3O_6 \cdot C_4H_6O_5$) | | | |
|---|---|---|---|
| | C (%) | H (%) | N (%) |
| Found: | 59.72 | 5.80 | 6.73 |
| Calculated: | 59.51 | 5.64 | 6.72 |

EXAMPLE 12

In 25 ml of acetone were dissolved 4.91 g of the crude free base of YM-09730 obtained in Reference Example 1 and 1.34 g of L-(−)-malic acid and the solution thus formed was stirred for 48 hours at 0° to 5° C. Crystals thus deposited were collected by filtration and washed with a small amount of cold acetone to provide 0.57 g of the L-(−)-malate of the dextro-rotatory optical isomer of diastereoisomer A of YM-09730. The specific rotation $[\alpha]_D^{20}$ was +78.3° (c=0.5, metahnol). Also, the specific rotation $[\alpha]_D^{20}$ of 0.44 g of the crystals obtained by recrystallizing the product from 50 times by volume of ethanol was +82.2° (c=0.5, methanol).

Melting point 190° to 191° C. (decomp.).

EXAMPLE 13

In 8 ml of chloroform was suspended 2.21 g of the L-(−)-malate of the dextro-rotatory optical isomer of diastereoisomer A of YM-09730 obtained in Example 11 and the suspension was treated, in succession, twice each time with 4.3 ml of a saturated aqueous sodium hydrogen carbonate solution, 4.3 ml of water, and then twice each time with 4.3 ml of 10% hydrochloric acid. The chlorofrom solution was dried over anhydrous magnesium sulfate and after filtration, the solution was evaporated to dryness under reduced pressure. The residue thus formed was dissolved in 3.5 ml of acetone and the solution thus formed was allowed to stand to provide 1.64 g of the hydrochloride of the dextro-rotatory optical isomer of diastereoisomer A of YM-09730 as deposits.

The specific rotation $[\alpha]_D^{20}$ was +11.65° (=0.5, methanol).

Melting point: 223° to 225° C. (decomp.)

| Elemental analysis (for $C_{27}H_{29}N_3O_6 \cdot HCl$) | | | | |
|---|---|---|---|---|
| | C (%) | H (%) | N (%) | Cl (%) |
| Found: | 61.35 | 5.55 | 8.01 | 6.96 |
| Calculated: | 61.42 | 5.73 | 7.96 | 6.71 |

| NMR (in $CD_3OD$, TMS internal standard, δ ppm): | |
|---|---|
| 1.80–2.70 | (2H, broad m, $C_4$—$H_2$) |
| 2.32, 2.34 | (6H, s, $C_{2,6}$—$CH_3$) |
| 3.0–4.0 | (4H, m, $C_{2',5'}$—$H_2$) |
| 3.64 | (3H, s, —$COOCH_3$) |
| 4.42 | (2H, s, —$CH_2\phi$) |
| 5.08 | (1H, s $C_4$—H) |
| 5.30 | (1H, m, $C_{3'}$—H) |
| 7.30–8.20 | (9H, m, H of benzene ring) |

EXAMPLE 14

In 5 ml of isopropanol were dissolved (S)-3-acetoacetoxy-1-benzylpyrroldine obtained by reacting 1.77 g of (S)-(−)-1-benzyl-3-hydroxypyrrolidine ($[\alpha]_D^{20}$ −3.77°, c=5, methanol) and 0.84 g of diketene for 3 hours at 70° to 80° C., 1.51 g of m-nitrobenzaldehyde and 1.15 g of 3-aminocrotonic acid methyl ester, and the solution was refluxed for 8 hours. The solvent was then distilled off under reduced pressure from the reaction mixture. The residue thus formed was dissolved in chloroform, the solution thus formed was washed, in succession, with a diluted hydrochloric acid, water, and then a saturated aqueous sodium hydrogen carbonate solution, and dried over anhydrous magnesium sulfate. Then, the solvent was distilled off under reduced pressure to provide 4.91 g of a mixture of the dextro-rotatory optical isomer of diastereoisomer A and the levo-rotatory optical isomer of diastereoisomer B of YM-09730 as a caramel. The crude free base thus obtained was applied to silica gel column chromatography column: Wakogel C-200, 2,000 g, eluent: ethyl acetate-acetic acid=6:1 v/v), whereby the oily acetate of the dextro-rotatory optical isomer of diastereoisomer A of YM-09730 showing a retention time of 28 min. by high-performance liquid chromatography.

The product was treated in chloroform with saturated aqueous sodium hydrogen carbonate and then diluted hydrochloric acid to provide 1.68 g of the hydrochloride of the dextro-rotatory optical isomer of diastereoisomer A of YM-09730. The specific rotation $[\alpha]_D^{20}$ was +116.5° (c=0.5, methanol).

EXAMPLE 15

In 25 ml of chloroform was dissolved 4.9 g of the crude free base obtained as in Example 14 and after adding thereto 15 ml of 10% hydrochloric acid, the resultant mixture was stirred well. Then, the organic layer thus formed was separated, washed again with 10 ml of 10% hydrochloric acid, and dried over anhydrous magnesium sulfate. Thereafter, the solvent was distilled off under reduced pressuer, the residue thus formed was dissolved in 10 ml of acetone, and the solution was allowed to stand for 2 days at 4° C. to provide 2.7 g of the hydrochloride by collecting the crystals thus deposited. For removing the levo-rotatory optical isomer of diastereoisomer B therefrom, the product thus obtained was treated with saturated aqueous sodium hydrogen carbonate in chloroform to form a free base and after adding 0.68 g of L-(-)-malic acid in 15 ml of ethanol, the resultant mixture was allowed to stand for 2 days at 4° C. Crystals thus deposited were collected by filtration and recrystallized from ethanol to provide 1.33 g of the L-(-)-malate of the dextro-rotatory optical isomer of diastereoisomer A of YM-09730 showing a retension time of 28 min. by high-performance liquid chromatography. The specific rotation $[\alpha]_D^{20}$ was +82.1° (c=0.5, metnaol).

EXAMPLE 16

In 5 ml of chloroform was suspended 1.25 g of the L-(-)-malate of the dextro-ratotory optical isomer of diastereoisomer A of YM-09730 and the suspension thus obtained was treated, in succession, twice each time with 3 ml of saturated aqueous sodium hydrogen carbonate and then twice each time with 3 ml of water. The chloroform solution was dried over anhydrous magnesium sulfate and then the solvent was distilled off under reduced pressure. To the residue thus formed was added 6 ml of ethanol and the mixture was allowed to stand overnight at 5° C. to provide 0.84 g of the crystals of the free base of the dextro-rotatory optical isomer of diastereoisomer A of YM-09730.

Melting point 138° to 140° C.

| Elemental analysis (for $C_{27}H_{29}N_3O_6$) | | | |
|---|---|---|---|
| | C (5) | H (%) | N (%) |
| Calculated: | 65.98 | 5.95 | 8.55 |
| Found: | 66.04 | 5.96 | 8.51 |

| NMR (in $CDCl_3$ TMS internal standard, $\delta$ ppm) | |
|---|---|
| 1.40 to 3.0 | (6H, m, $C_{2',4'5'}$—$H_2$) |
| 2.34, 2.36 | (6H, s, $C_{2,6}$—$CH_3$) |
| 3.65 | (5H, s, —$COOCH_3$ and —$CH_2\phi$) |
| 5.10 | (1H, s, $C_4$—H) |
| 5.12 | (1H, m, $C_3$—H) |
| 5.78 | (1H, broad s, —NH) |
| 7.16 to 8.24 | (9H, m, H of benzene ring). |

| Formulation Example 1 (Tablet) | | |
|---|---|---|
| | One tablet | 5,000 tabs. |
| Isomer A hydrochloride | 10.0 mg | 50 g |
| Lactose | 101.0 mg | 502 g |
| Corn starch | 25.3 mg | 126.5 g |
| Hydroxypropyl cellulose | 3.0 mg | 15 g |
| Magnesium stearate | 0.7 mg | 3.5 g |
| | 140 mg | 700 g |

To a uniform mixture of 50 g of the hydrochloride of isomer A, 502 g of lactose, and 126.5 g of corn starch was added 150 g of an aqueous 10% hydroxypropyl cellulose and the mixture was kneaded and granulated. After drying, 3.5 g of magnesium stearate was added to the granules and they were uniformly mixed and then formed into tablets each of 140 mg.

| Formulation Example 2 (Capsule) | | |
|---|---|---|
| | One capsule | 1,000 cap. |
| Isomer A hydrochloride | 10.0 mg | 10 g |
| Crystal lactose | 189.0 mg | 189 g |
| Magnesium stearate | 1.0 mg | 1 g |
| | 200 mg | 200 g |

The above components were uniformly mixed and 200 mg thereof was filled in each capsule to provide capsule medicaments.

| Formulation Example 3 (Injection) | |
|---|---|
| Isomer A hydrochloride | 1 mg |
| D-sorbitol | 100 mg |

The above components were dissolved in distilled water for injection and after adjusting the pH thereof to 4 by the addition of hydrochloric acid, distilled water for injection was added to make the total volume to 2 ml.

What is claimed is:

1. A process of producing diastereoisomer A or a pharmaceutically acceptable acid addition salt thereof which comprises subjecting a mixture of diastereoisomers A and B of 2,6-dimethyl-4-(3-nitrophenyl)-1,4-dihydropyridine-3,5-dicarboxylic acid 3-(1-benzylpyrrolidin-3-yl) ester 5-methyl ester to column chromatography using silica gel as a carrier and a mixture of ethyl acetate and acetic acid as an eluent, and then separating the acetate of diastereoisomer A from the eluate, or treating the acetate with a base, or further treating the resulting diastereoisomer A with a pharmaceutically acceptable acid.

2. A process of producing the dextro-rotatory optical isomer of diastereoisomer A which comprises subjecting a mixture of diastereoisomers A and B of 2,6-dimethyl-4-(3-nitrophenyl)-1,4-dihydropyridine-3,5-dicarboxylic acid 3-(1-benzylpyrrolidin-3-yl) ester 5-methyl ester to column chromatography using silica gel as a carrier and a mixture of ethyl acetate and acetic acid as an eluent, separating the acetate of diastereoisomer A from the eluate, treating the acetate with a base, and then reacting resulting diastereoisomer A with L-(-)-malic acid to depoist the L-(-)-malate of the dextro-rotatory optical isomer of diastereoisomer A, or treating the L-(-)-malate with a base, or further treating the resulting dextro-rotatory optical isomer with a pharmaceutically acceptable acid.

* * * * *